United States Patent [19]
Wiggins

[11] 4,391,373
[45] Jul. 5, 1983

[54] METHOD OF AND APPARATUS FOR COMPENSATING SIGNAL DRIFT DURING CONTAINER INSPECTION

[75] Inventor: Edmund C. Wiggins, Pinellas County, Fla.

[73] Assignee: Barry-Wehmiller Company, St. Louis, Mo.

[21] Appl. No.: 205,600

[22] Filed: Nov. 10, 1980

[51] Int. Cl.³ .................... G01N 21/32; G06M 7/00; H01J 39/12
[52] U.S. Cl. ................. 209/526; 209/588; 250/223 B; 356/240
[58] Field of Search ............. 209/523, 524, 526, 588; 250/252, 223 B; 356/237, 239, 240

[56] References Cited

U.S. PATENT DOCUMENTS

| | | | |
|---|---|---|---|
| 3,267,796 | 8/1966 | Mathias | 88/14 |
| 3,327,849 | 6/1967 | Sorbie | 209/111.7 |
| 3,349,906 | 10/1967 | Calhoun | 209/111.7 |
| 3,355,980 | 12/1967 | Mathias | 88/14 |
| 3,479,514 | 11/1969 | Kidwell | 250/223 |
| 3,631,255 | 12/1971 | Gender et al. | 250/223 |
| 3,918,564 | 11/1975 | Heiman et al. | 194/100 A |
| 3,991,605 | 11/1976 | Reuland | 209/535 X |
| 4,136,930 | 1/1979 | Gomm et al. | 356/240 X |
| 4,213,042 | 7/1980 | Beach et al. | 209/526 X |
| 4,300,689 | 11/1981 | Franklin et al. | 209/524 |

FOREIGN PATENT DOCUMENTS 2003268 8/1977 United Kingdom .

Primary Examiner—David A. Scherbel
Attorney, Agent, or Firm—Gravely, Lieder & Woodruff

[57] ABSTRACT

A method of and apparatus for compensating for signal drift in container inspection apparatus using radiant energy emitters and detectors for scanning the containers in combination with a processing circuit associated with the emitters and detectors for synchronizing the scanning signals and processing the signals in subcircuits such that the signals generated during intervals when no container is being scanned are constantly being examined for drift and signals compensated for drift, if any, are used for comparison with container inspection scan signals to determine if a container needs to be rejected.

4 Claims, 5 Drawing Figures

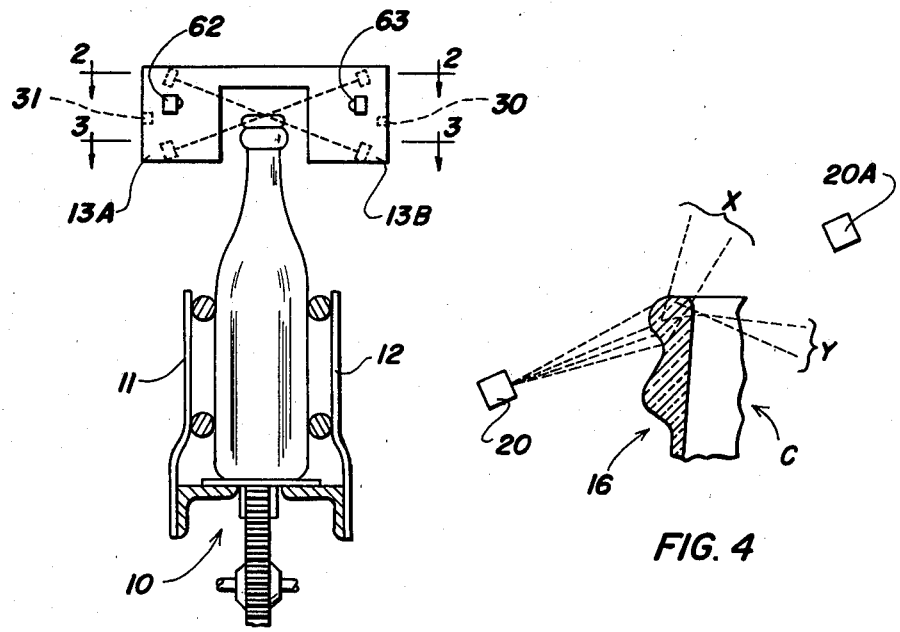
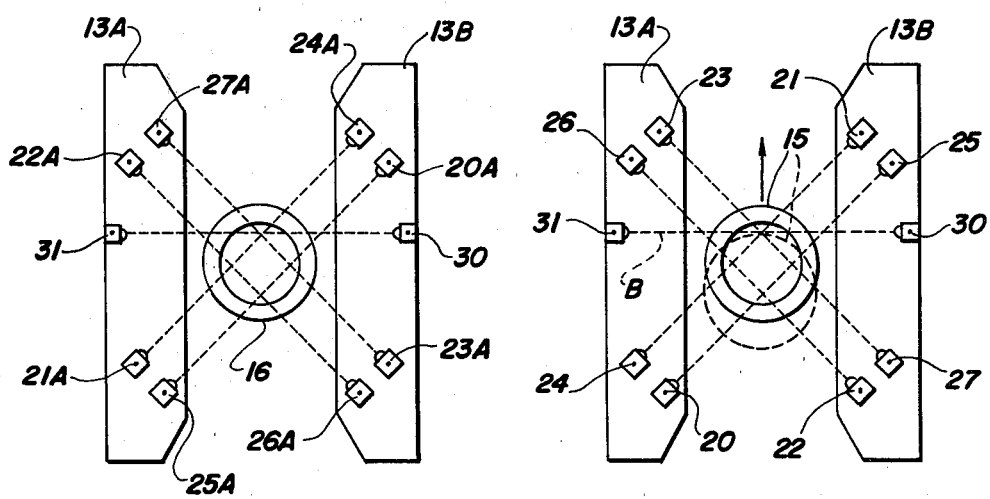
FIG. 1
FIG. 4
FIG. 2
DETECTORS
FIG. 3
EMITTERS

METHOD OF AND APPARATUS FOR COMPENSATING SIGNAL DRIFT DURING CONTAINER INSPECTION

BACKGROUND OF THE INVENTION

1. Field of the Invention

This invention relates to a method of and apparatus for compensating signal drift during inspecting of the crown ring of containers for detecting chips and other defects which render containers unfit for use.

2. Description of the Prior Art

The existing apparatus for detecting chips and defects in container crown rings that uses infrared beams is subject to errors which reduce performance below the theoretical capability thereof. The errors arise because fixed threshold is used in the detector circuit. The sensitivity of the detector must be reduced from the maximum so that there will not be an unacceptable high false rejection rate due to component drift. This drift may arise because LED output efficiency changes with temperature and aging, or transistor gain changes with temperature, or transistor output changes due to ambient light variations, or detector threshold changes with temperature, or LED current changes due to changes in the drive resistors caused by high power, aging, humidity and temperature, or buildup of dirt and moisture on the protective windows which reduces the light reaching the phototransistor. Moreover, if a single threshold value is used, all LED phototransistors channels must track as they drift or imbalances will arise. There are many variables involved which makes any drift cancellation technique extremely complicated.

The pertinent prior art includes the prior U.S. Pat. No. 4,213,042 of Beach and Smith which issued July 15, 1980 and is commonly assigned with this application. This patent discloses emitters and receivers in cooperating pairs to scan an entire crown ring, electronic control means driving the emitters, sequential driver circuits and synchronous detector circuits, and means to trigger a reject device.

The published British patent application No. 2,003,268A, dated Mar. 7, 1979, discloses a method of inspecting transparent objects by projecting infrared radiation onto the object, detecting the emerging beam, and applying synchronous control circuits for scanning the sources and detectors.

The commonly assigned patent of Gender et al., U.S. Pat No. 3,631,255 of Dec. 28, 1971 has disclosed a crown ring inspection apparatus which includes photoelectric means for examining transparent containers in association with an optical projector for presenting the container image to a photomultiplier tube which develops electrical signals suitable for operating a reject mechanism.

The prior art includes Calhoun et al. U.S. Pat. No. 3,349,906 of Oct. 31, 1967; Kidwell U.S. Pat. No. 3,479,514 of Nov. 18, 1969; Mathias U.S. Pat. Nos. 3,267,796 of Aug. 23, 1966, and 3,355,980 of Dec. 5, 1967; and Sorbie U.S. Pat. No. 3,327,849 of June 27, 1967.

BRIEF DESCRIPTION OF THE INVENTION

The present invention is an improvement over the detector of the prior Beach et al patent and resides in a method and apparatus for providing automatic compensation in threshold values as applied to a chipped finish detector to obtain greater accuracy of the detection of crown ring defects in containers.

The automatic compensation for container chipped finish detectors is directed to compensating for drift in the signal strength from detectors. It has been observed that virtually no drift occurs during the time between successive container inspections, even when the time between container inspections varies from 50 ms at 1200 containers per minute to 0.5 sec. at 120 containers per minute. The current amount of the drift may be determined by measuring the output of the detector channels during each interval when containers are not present in the inspection zone. During the time between inspections there is an interval when each detector channel is unaffected by the containers, so by measuring the channel output during this interval, the change can be used to adjust the detecting threshold during the next inspection, and a continuous and automatic compensation is obtained.

It is recognized that certain kinds of container defects are difficult to detect with infrared beam type detectors. Most notably, chip type defects that do not break completely through the sealing ring, such as inside or outside chips, are difficult to detect. Since these result in "thin spots" in the sealing ring there is still some material left to absorb, reflect or refract a portion of the beam. Because of drift, detectors must normally be set so that only a gross change in the amount of infrared transmitted from the detector is detected. With compensation, changes in transmission of only a few percent may be easily and accurately detected. This allows detection of many kinds of chips that allow only partial transmission of the beam.

Infrared beam detectors have been primarily applied to the detection of chips in crown type finishes. This is because the curved sealing ring diffuses/refracts the beam so that virtually no infrared reaches the detector, even with flint glass. Other applications for infrared beam detectors have been with dark screw thread containers, where the material absorbs most of the infrared, and with screw thread type finishes with very close pitched threads. The presence of several threads in one beam disperses most of the light and the effect is enhanced in dark containers. The standard type of screw thread has the characteristic that the inside and outside of the container is nearly parallel, and very little lensing of the infrared beam occurs. Also the wide spiral thread results in clear areas, so that some detector channels do not have a thread present in the beam and almost none of the beam is dispersed. When this finish is used in a flint glass container, the transmission through the finish may exceed 90% in places. By being able to detect small changes in the amount of infrared transmission, such as 90% with good finish as compared to 100% with a completely broken through finish, the same apparatus can be used to inspect all screw thread and crown type finishes.

The objects of the present invention are to provide separate thresholds for each detector, and to provide automatic updating of the threshold signal values to maintain a substantially constant detection performance.

A further object is to incorporate automatic compensation so that no initial set up or balancing is required for the detectors, and changes in transmission on only a few percent may be easily and substantially accurately sensed, whereby chips in the crown ring that allow only partial transmission of the emitter beam may be detected.

Another object of the present invention is to provide a method for detecting the kinds of crown ring chips which do not break completely through the sealing ring, either inside or outside, and form thin spots which improve upon older infrared detectors which have to be set so that only a gross change in the amount of infrared transmitted can be detected.

A presently preferred embodiment of the invention comprises pulsed infrared emitters illuminating designated areas of containers, such as the crown ring area of a transparent container, while in motion to find objectionable defects, cooperating detectors responsive to the infrared radiation used to illuminate such defects, and electronic circuitry associated with the emitters and detectors for providing separate automatically updated threshold signal levels for direct comparison with the signal value output from container inspection by the detectors so that the result of the comparison can be applied, when necessary, to control a reject mechanism.

BRIEF DESCRIPTION OF THE DRAWINGS

A preferred embodiment of the present invention may be illustrated in the accompanying drawings, wherein:

FIG. 1 is a schematic elevation of a conveyor for conveying containers through an inspection zone where the crown finish may be subjected to inspection for detection of defects;

FIG. 2 is a diagrammatic view taken along line 2—2 in FIG. 1 to illustrate the arrangement of detectors distributed around the container crown finish when moved into and through the inspection zone;

FIG. 3 is a view similar to FIG. 2, but taken along line 3—3 in FIG. 1 to show the arrangement of emitters paired with the detectors;

FIG. 4 is a diagram of the pattern of the beam in relation to the lens action of the container crown finish.

DETAILED DESCRIPTION OF THE EMBODIMENT

Figure 5:
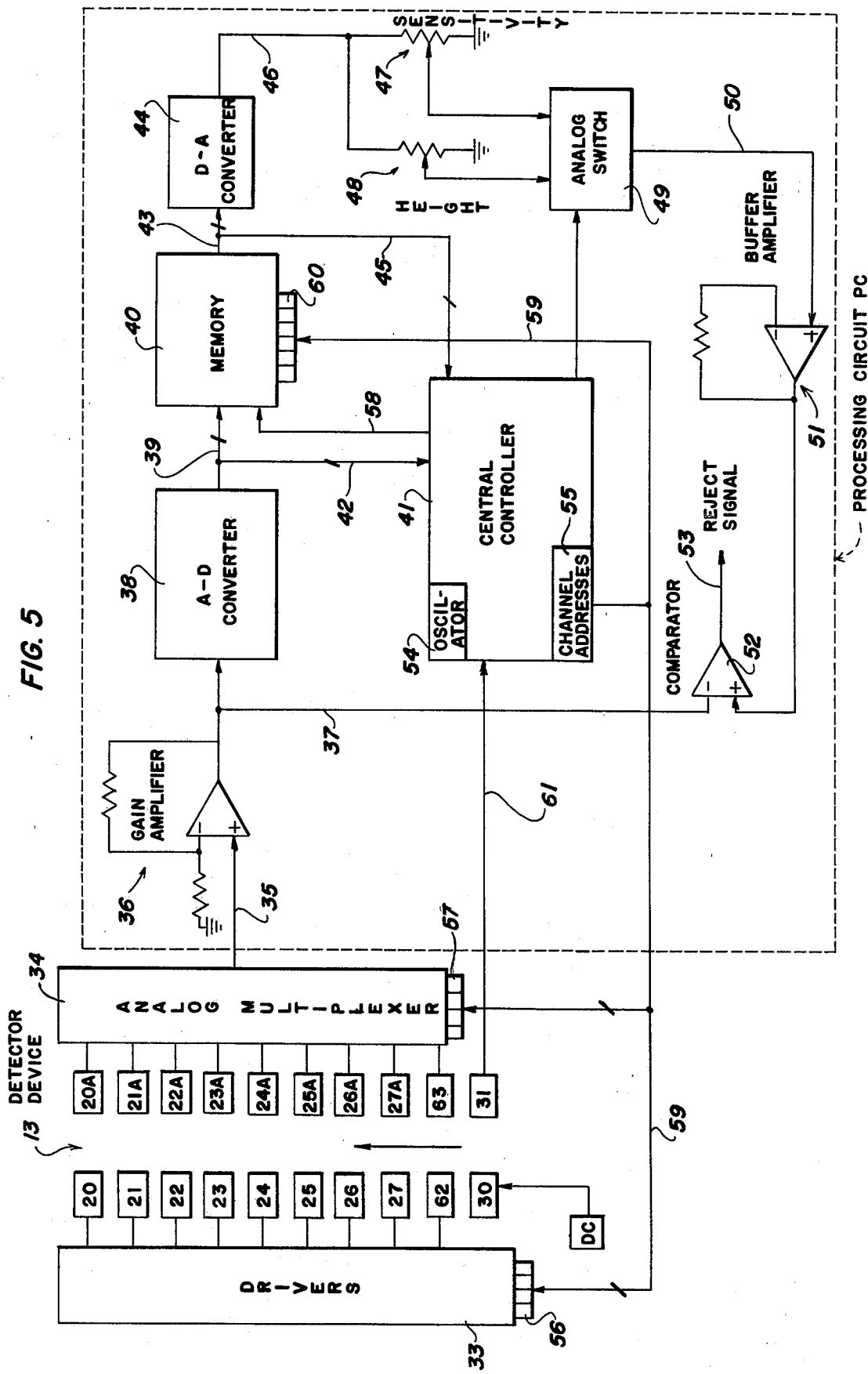
FIG. 5 is a block diagram of the electronic circuitry and components contained therein, all of which is associated with the arrangement of the inspection zone seen in FIG. 1.

In FIG. 1, there is shown in somewhat abbreviated form a conveyor 10 and side guides 11 and 12 for keeping a line of containers C in a set path past a station where a crown ring chip detector device 13 is located by suitable support means (not shown) in position to straddle the crown rings as they pass through the station. The device 13 includes housings 13A and 13B in which are mounted the components to be described below. Any suitable conveyor apparatus may be employed, and at a suitable location beyond the inspection station a reject device (not shown) can be installed for removing containers found to be defective or unacceptable.

The internal means contained in housings 13A and 13B of the detector device 13 is seen in FIG. 2 and 3. The installation herein preferred locates eight infrared light emitters 20 and 27 (FIG. 3) below the level of the crown ring portion 16 and the detectors above that portion 16 (FIG. 2). The detector means 20A to 27A are shown in an arrangement where the leading edge 15 of the crown ring portion 16 is inspected first followed by the inspection of the trailing edge, and thereafter the areas between these edges are inspected. For the indicated direction of container movement in FIG. 3, the activation of the emitters is in the order of emitters 20, 21, 22, 23 to catch the leading and trailing edges of the container. Then in order the activation follows for emitters 24, 25, 26 and 27. In the event that the crown ring is chipped, a portion of the infrared light beam will pass beyond the crown ring and activate the detector positioned in line with the projected beam. Infrared emitting diodes and phototransistors are used because of their fast rise and fall times but visible light devices could be used with success at lower speeds.

The view of FIG. 4 is intended to illustrate an acceptable arrangement for the respective emitters, such as emitter 20 to be angled upwardly from the horizontal at approximately 1220 . However, this angle may vary from about 10° to about 15°. The lens action of the crown ring on the container C is such that if there is no chip imperfection the infrared light beam will be scattered as shown by the dotted lines X and Y. On the other hand, if there is a chip imperfection in the crown ring, some of the infrared light beam will pass beyond and be intercepted by the detector 20A which is paired with the emitter 20. Test results have shown that a chip of approximately $\frac{3}{8}$" in the crown ring can be detected almost every time. If the chip size gets smaller the detection achievement decreases until a chip size of $\frac{1}{8}$" can be detected approximately half the time. With containers that characteristically absorb infrared light, the detection threshold of the detectors may be set at a lower level so as to improve detection of small sized chips. At the lower levels, however, false rejections can be experienced when containers having high infrared transmission characteristics reach the inspection station. This feature is provided for by setting the detector thresholds so they ignore a minimum transmission level.

The disposition of the emitters and the paired detectors, as seen in FIGS. 3 and 2 respectively, is such that the emitter beams impinge on the crown ring area at eight substantially equally spaced target sectors. The beams have a spread angle of about 10° so that with eight beams the entire crown ring can be irradiated with infrared light. As shown in FIG. 4, detector 20A is located on the center line of the beam from its paired emitter 20.

In order to trigger the detector device 13 into action, each time a container enters the inspection station, the leading edge 15 of the crown ring 16 breaks a light beam B which is established between a light source 30 energized from a DC power source and a photocell 31. The photocell 31 transmits a signal to a timing start device located in and a part of the controller 41. The duration of the time period may be as short as one millisecond so that a complete scan of the crown ring of each container C can be obtained.

Referring now to FIG. 5, there is illustrated the block diagram of the electronic circuitry and components for controlling the automatic compensation for the detector system utilized in the inspection of the container chipped finish to determine the presence or absence of defects. In that diagram, there is shown schematically the plurality of emitters at 20 through 27. These emitters are suitably connected into a driver circuit 33 wherein each of the emitters is provided with its own driver circuit or address. The emitters are in cooperative alignment with an equal number of detectors indicated at 20A through 27A. The detectors are connected into a suitable circuit arrangement at 34 so as to provide each of the detectors with its particular address. The circuits at 34 may be of the analog multiplexer type so that as each detector is activated by a beam from the cooperative emitter, a signal is broadcast through lead 35 into a processing circuit PC where the desired signals from the detector device 13 are processed to determine whether a container must be rejected or allowed to pass. Frequent reference will be made to the components in the processing circuit PC and to the detector device 13.

The lead 35 is connected into a gain amplifier 36 of the usual type to raise the strength of the signal to a usable value, and from the amplifier the signals are directed to a branch 37, to be referred to presently, as well as being admitted to an analog-digital converter 38, hereinafter referred to as the A-D converter. The individual signals from the A-D converter 38 are then conducted through leads 39 into a memory device 40, as well as into a central controller 41 through leads 42. The memory device 40 is connected through leads 43 to a digital-analog converter 44, hereinafter referred to as a D-A converter and also through leads 45 to the central controller 41. The output 46 from the D-A converter 44 is connected into a manually adjustable chip sensitivity potentiometer 47, as well as into a container over-height sensitivity potentiometer 48. These potentiometers direct the adjusted signals into an analog multiplexer switch 49, and the output 50 is connected into a buffer amplifier circuit 51, and then into one side of a comparator 52. The output from the analog switch 49 is a predetermined threshold signal value which may be about 80% of the strength of the incoming signal from the D-A converter 44. The output from the gain amplifier 36 is also conducted by lead 37, as mentioned above, into the other terminal of the comparator 52 so that if the strength of the signal in lead 37 is greater than the threshold signal from the buffer amplifier circuit 51, a reject signal is generated at lead 53 for operating a suitable reject mechanism (not shown) which effectively removes the proper container from the conveyor 10 at a suitable point downstream from the location of the detector device 13.

The central controller 41 regulates the above described circuitry since it contains an oscillator 54 which is a suitable device for timing the action of the emitters and the responses of the detectors in an orderly fashion by means of the address selecting circuits 55 associated with the corresponding addresses 56 for the driver circuit 33 for the emitters 20-27 and corresponding addresses 57 associated with the detectors 20A-27A. It is also seen in FIG. 5 that the central controller 41 is connected to the memory device 40 by lead 58 (the read/write control) so as to regulate its responses between the memory of the incoming signals and storing them in the proper address, and releasing the signals when it is desired to feed them through the D-A converter 44 for eventual comparison at the comparator device 52 with the corresponding signal reaching the comparator through lead 37. The controller address selecting circuit 55 is connected by leads 59 into the address selecting means 60 in the memory 40, as well as for the address means 56 and 57.

It should now be apparent that the circuit PC arrangement of FIG. 5 provides means which directs each emitter 20 through 27 to project a beam toward each cooperatively related detector 20A through 27A with a pulsed light beam at a time when either no part of a container is passing between the cooperative emitters and detectors or at a time when the containers are passing through the pulsed light beam. In order to sense these two control situations, the timing device 30-31 will signal the central controller 41 by lead 61 each time a container passes through the inspection device 13. In this way, the controller 41 knows which mode of operation exists as between the emitters and detectors. The resulting radiant energy pulses received at each detector are processed in a first subcircuit. The first subcircuit operates to convert the detector signals from analog to digital form and stores them in the electronic memory device 40 at its particular address which corresponds to the signal generated by each of the detectors 20A through 27A.

The storage of signals in memory 40 proceeds at the direction of the central controller 41 as long as no containers are supplied for inspection. In this mode, the emitters and detectors function continuously during the period when no container is passing through the inspection zone of device 13, as well as when containers are actually being inspected. As will be pointed out presently, the electronic memory device 40 is cleared of its memorized signals after every container inspection period so that if there is a decrease change in the value of the signal, the memory can accommodate such change. Each emitter and detector combination performs a scan every 192 microseconds, but when a container reaches the inspection zone, it is sensed by the timing signal device 30-31 and the central controller 41 is thereby advised of that appearance of a container and increases the scanning rate to 128 microseconds so as to minimize the effects of container motion. Concurrently, the central controller 41 switches the memory device 40 from the write mode to the read mode, and also provides the memory device with the proper address corresponding to the detector 20A through 27A which is activated. The signal output from the memory device 40, after being converted to analog form, is applied to the input of the manually adjustable sensitivity control means 47 and 48 of a second subcircuit.

It has been pointed out above that the processing circuit operates in two different modes which may be referred to as the calibrating mode and the inspection mode. In the calibrate mode, the central controller 41 continuously causes the emitters 20 through 27 and the detectors 20A through 27A to scan, one cooperative pair thereof performing its scan every 192 microseconds. The maximum signal transmission occurs when no container is present at the inspection zone 13, and it is stored at the proper address in the memory device 40. This constant updating of the signal values in the memory device 40 avoids having a timing signal that indicates when no containers are present in the zone. The central controller 41 zeros each address in the memory device 40 after each inspection mode so that a new maximum may be generated prior to the next inspection. In this way, the new maximum signal value could be less than the old maximum value if any drift had occurred in the system.

In the inspection mode, the central controller causes scanning of each emitter-detector pair when the signal is received from the timing device 31. Each pair is scanned every 128 microseconds which is at a faster rate than before, and keeps the inspection time for eight chip detectors down to 1.024 microseconds, while 192 microseconds provides extra time during the calibrate method for the A-D conversion process. No A-D conversion is accomplished during the inspection mode. The maximum signal strength stored in the memory device 40 when no containers are in the inspection zone represents 100% transmission for each address associated with the emitter-detector pairs. In the second subcircuit means, a percentage, such as about 80% of this maximum transmission is applied at one terminal of the comparator 52 through manipulation of the sensitivity potentiometer 47 so as to predetermine the threshold signal value. If this threshold value is maintained for the signals generated at each address, and if all the transmitted signals have a value greater than the threshold signal value, a reject signal would be generated at the output 53. However, if the signal value is less than the threshold signal value, the comparator 52 will not generate a reject signal at its output 53.

As shown in FIG. 1, the detector device 13 is provided with a special emitter 62 and a receiver 63 for the purpose of detecting containers that are too tall. A too tall container will break the radiant beam emitted by emitter 62 and generate a signal response in receiver 63 through a suitable inverter not necessary to show. Such an inverter is well known and reverses the logic so that the receiver 63 has not output at the time of inspection, determined by the signal from the detector 31. The emitter 62 is connected into the driver 33 so as not to lose synchronization with the system, while the receiver 63 is connected to the analog multiplexer 34 for the same reason.

The foregoing specification has set forth a method of operating a container inspection apparatus in which a detector device 13 is able to generate signals individually from a plurality of emitter-detector pairs, which signals are generated in timed relation when containers are being inspected and during the occurence of the space or interval between the containers passing the inspection zone. A processing circuit PC is connected with the detector device 13 through a first subcircuit so that a memory is operated to store signals generated during the intervals between containers and responds when called upon to release the stored signal values which are passed through a second subcircuit which includes a sensitivity control and analog switch 47-49, and a circuit containing a buffer amplifier 51 so as to arrive at the comparator 52 when the next container inspection signal arrives at the comparator. In this way, if there is a change or drift in the value of the signals memorized during the intervals between actual container inspection, the changed signal value is used to adjust a threshold value which is compared with the container inspection signal value. The processing circuit PC automatically compensates for any drift in the signal values which may be the result of dirt or loss of strength of the components, or the effects of the environments in which the apparatus is situated.

What is claimed is:

1. In apparatus for the inspection of containers movable through an inspection zone, said apparatus having a plurality of radiant energy beam emitters and detectors oriented on the container passage in the inspection zone, such that said emitters and detectors are aligned in cooperating pairs to produce output signals from said detectors corresponding to container inspection values and to values during intervals between container movement through the inspection zone, the improvement of processing circuit means connected to said emitters and detectors including:

(1) subcircuit means for storing the signal values generated each time during intervals between container movement in the inspection zone and means for adjusting the stored signal values to generate threshold signal values, said subcircuit means comprising an analog to digital signal converter, a memory circuit means connected to said analog to digital output, and a digital to analog signal converter, and (2) subcircuit means for comparing the output signal values from said detectors during each container inspection directly with said adjusted threshold signal values, whereby each output of the analog to digital signal converter is compared with the value of the signal previously stored in said memory circuit means for determining the need to update the stored signal values for signal drift compensation.

2. In apparatus for the inspection of containers movable through an inspection zone, said apparatus having a plurality of radiant energy beam detectors oriented on the container passage in the inspection zone, such that said emitters and detectors are aligned in cooperating pairs to produce output signals from said detectors corresponding to container inspection values and to values during intervals between container movement through the inspection zone, the improvement of processing circuit means connected to said emitters and detectors including:

(1) subcircuit means for storing the signal values generated each time during intervals between container movement in the inspection zone and means for adjusting the stored signal values to generate threshold signal values, and (2) subcircuit means for comparing the output signal values from said detectors during each container inspection directly with said adjusted threshold signal values, wherein said second mentioned subcircuit means comprises a signal comparator circuit having one input terminal connected to said radiant energy beam detectors for introducing such signal values, and a sensitivity control circuit connected between a second input terminal of said comparator circuit and said first mentioned subcircuit means for introducing the compensated signal values to be compared with said detector output signal values.

3. In the apparatus according to claim 2, the further improvement wherein said sensitivity control circuit is adjustable for selecting compensated signal values as a percentage of the uncompensated signal value.

4. An automatic signal compensation arrangement for a container chipped finish detector having means for moving a series of containers through a detection zone, said compensation arrangement comprising:

(a) emitters and detectors arranged in cooperative pairs in the detection zone to generate signals in the absence of containers and to inspect the container crown finish and generate signals with respect thereto;

(b) a processing circuit for said signals generated by said emitters and detectors, including:

(1) a first subcircuit containing a signal receiving analog to digital converter connected to said detectors, a memory, and a signal output digital to analog converter;

(2) a controller connected to said memory for discriminating between signals from said detectors in the cooperative pairs generated from container inspection and signals generated during intervals between container inspection so as to establish separation of the signals received by the memory from the analog to digital converter;

(3) a second subcircuit containing a threshold signal control and a signal comparator for using the signals stored in said memory during intervals between container inspection for adjusting the threshold signal values for detector signal drift; and (c) a reject signal circuit connected into said signal comparator for receiving a reject signal each time the detector signal values are greater than the adjusted threshold signal values.

* * * * *

UNITED STATES PATENT AND TRADEMARK OFFICE
CERTIFICATE OF CORRECTION

PATENT NO. : 4,391,373
DATED : July 5, 1983
INVENTOR(S) : Edmund C. Wiggins

It is certified that error appears in the above-identified patent and that said Letters Patent is hereby corrected as shown below:

Column 2, line 66, cancel "on only" and substitute therefor "of only".

Column 3, line 64, cancel "20 and 27" and substitute therefor "20 to 27".

Column 4, line 17, cancel "1220" and substitute therefor "12°".

Signed and Sealed this

Twentieth Day of September 1983

[SEAL]

Attest:

Attesting Officer

GERALD J. MOSSINGHOFF

Commissioner of Patents and Trademarks